United States Patent
Hofmann et al.

(10) Patent No.: US 8,013,095 B2
(45) Date of Patent: Sep. 6, 2011

(54) RU SULFOXIDE COMPLEXES, THEIR PREPARATION AND USE

(75) Inventors: Marco Hofmann, Burghausen (DE); Hans-Juergen Elberle, Munich (DE)

(73) Assignee: Wacker Chemie AG, Munich (DE)

(*) Notice: Subject to any disclaimer, the term of this patent is extended or adjusted under 35 U.S.C. 154(b) by 0 days.

(21) Appl. No.: 12/997,749

(22) PCT Filed: May 25, 2009

(86) PCT No.: PCT/EP2009/056314
§ 371 (c)(1), (2), (4) Date: Dec. 13, 2010

(87) PCT Pub. No.: WO2009/150033
PCT Pub. Date: Dec. 17, 2009

(65) Prior Publication Data
US 2011/0098435 A1    Apr. 28, 2011

(30) Foreign Application Priority Data
Jun. 11, 2008 (DE) .......................... 10 2008 002 364

(51) Int. Cl.
*C08G 77/08* (2006.01)
*C08G 77/12* (2006.01)

(52) U.S. Cl. ........................................... 528/15; 528/31

(58) Field of Classification Search ........................ None
See application file for complete search history.

(56) References Cited

U.S. PATENT DOCUMENTS

| | | |
|---|---|---|
| 3,715,334 A | 2/1973 | Karstedt |
| 3,775,452 A | 11/1973 | Karstedt |
| 4,309,558 A | 1/1982 | Koga et al. |
| 5,248,802 A | 9/1993 | Bank |
| 5,559,264 A | 9/1996 | Bowman et al. |
| 2004/0092759 A1 | 5/2004 | Westmeyer et al. |
| 2009/0069524 A1 | 3/2009 | Hofmann et al. |
| 2009/0171056 A1 | 7/2009 | Hofmann et al. |

FOREIGN PATENT DOCUMENTS

| | | |
|---|---|---|
| DE | 2810032 A1 | 9/1978 |
| DE | 102006017588 A1 | 10/2007 |
| DE | 102006017594 A1 | 10/2007 |
| EP | 0403706 A2 | 12/1990 |

OTHER PUBLICATIONS

Nagashima et al. "Oxidative Addiiton of Allylic Halides to Ruthenium (II) Compounds. Preparation, Reactions, and X-ray Crystallographic Structure of Ruthenium (IV)-Allyl Complexes", Organometallics, 1990, 9, 799-807.*

Walter Noll: "Chemie und Technologie der Silicone (Chemistry and Technology of Silicones", Verlag Chemie GmbH, Weinheim/Bergstrasse 1968, cited in the appication, an English Abstract is enclosed.

Bogdan Marciniec: "Comprehensive Handbook on Hydroxysilylation," Oxford: Pergamon Press, 1992.

Wilkinson et al., J. Chem. Soc., Dalton Trans. 1973, p. 204 ff.

* cited by examiner

*Primary Examiner* — Robert Loewe
(74) *Attorney, Agent, or Firm* — Brooks Kushman P.C.

(57) ABSTRACT

Ru(0) complexes containing sulfoxide ligands and aliphatically unsaturated ligands are effective hydrosilylation catalysts useful in particular for addition curing organosilicon compositions.

7 Claims, No Drawings

RU SULFOXIDE COMPLEXES, THEIR PREPARATION AND USE

CROSS-REFERENCE TO RELATED APPLICATION

This application is the U.S. national phase of PCT Appln. No. PCT/EP2009/056314 filed May 25, 2009 which claims priority to German application DE 10 2008 002 364.7 filed Jun. 11, 2008.

BACKGROUND OF THE INVENTION

1. Field of the Invention

The present invention relates to novel Ru-sulfoxide complex catalysts, their preparation, their use in crosslinkable silicone compositions and also the silicone elastomers produced therefrom.

The addition of Si—H-functional compounds onto compounds having aliphatic unsaturated bonds, in particular C=C double bonds (hydrosilylation) has been known for a long time.

2. Description of the Related Art

Si-containing organic compounds, organosilanes and organopolysiloxanes can be prepared by hydrosilylation. Hydrosilylation is used, in particular, in the addition-crosslinking curing of organopolysiloxanes in the silicone industry, for example for the production of elastomers, impression-making compositions in the dental industry or antiadhesive coatings in the paper and films industry.

Platinum and compounds thereof are most frequently used as catalysts for the hydrosilylation reaction, with the platinum being used either in metallic form, as metal immobilized on an inorganic support, as a platinum salt or in the form of a soluble or insoluble platinum complex.

Up to now, the "Karstedt catalyst" which consists predominantly of a dimeric platinum-tetramethyldivinylsiloxane complex which can be described by the formula [Pt$_2$(TMDVS)$_3$] (TMDVS=tetramethyldivinyldisiloxane) and is known from U.S. Pat. No. 3,715,334 and U.S. Pat. No. 3,775,452 has been used for the majority of hydrosilylation reactions carried out in industry. The Karstedt catalyst is prepared from hexachloroplatinic acid H$_2$PtCl$_6$ which as an alcoholic solution is likewise frequently used as a hydrosilylation catalyst.

Since platinum is one of the most expensive noble metals, efforts have frequently been made to use other metals and compounds thereof as catalysts in hydrosilylation. Thus, the use of the other platinum group metals Pd, Rh, Ir, Ru in hydrosilylation is already known from the prior art. However, these have been described as alternatives to Pt mainly as catalysts for use in the case of specific substrates.

Thus, for example, US 2004/0092759 A1 and U.S. Pat. No. 5,559,264 describe Ru catalysts such as RuCl$_3$, RuBr$_3$, Ru(acac)$_3$, Ru/C, Ru$_3$(CO)$_{12}$, [RuCl$_2$(CO)$_3$]$_2$, [Ru(COD)Cl$_2$]$_n$ (COD=1,5-cyclooctadiene), Ru(PPh$_3$)$_2$(CO)$_2$Cl$_2$ and Ru(PPh$_3$)$_3$(CO)H$_2$ for the hydrosilylation of HSi(R)$_x$(OR)$_{3-x}$ (x=0-2) with an olefinic halide such as allyl chloride.

EP 0403706 A2 describes the use of Ru complexes having at least one tertiary phosphine ligand, for example Ru(CO)$_3$(PPh$_3$)$_2$, RuCl$_2$(PPh$_3$)$_2$, Ru(H)(Cl)(PPh$_3$)$_3$, Ru(PPh$_3$)$_4$H$_2$ and Ru(CH$_2$=CH$_2$)(PPh$_3$)$_3$, as catalysts for the hydro-silylation of allylamines by means of SiH-functional silanes.

U.S. Pat. No. 5,248,802 describes the hydrolysilylation of trichlorosilane with olefinic nitriles, e.g. acrylo-nitrile, in the presence of Ru-halogen or Ru-phosphine compounds such as RuCl$_3$, RuBr$_3$, RuI$_3$, Ru(CO)$_3$(PPh$_3$)$_2$, RuCl$_2$(PPh$_3$)$_3$, Ru(H)(Cl)(PPh$_3$)$_3$, RuH$_2$(PPh$_3$)$_4$, Ru(CH$_2$=CH$_2$)(PPh$_3$)$_3$ and RuCl$_2$(CO)$_2$(PPh$_3$)$_2$.

Finally, DE 2810032 A1 describes the hydrosilylation of dichlorosilane with olefins in the presence of Ru complexes such as RuCl$_2$(PPh$_3$)$_3$, Ru(H)(Cl)(PPh$_3$)$_3$, RuH$_3$(PPh$_3$)$_3$[Si(OMe)$_3$], RuH$_3$(PPh$_3$)$_3$[Si(OMe)$_2$Ph] and RuH$_2$(PPh$_3$)$_4$.

However, these catalysts are generally significantly inferior to the customary Pt catalysts with respect to reactivity and selectivity. The rate and selectivity of the non-Pt catalysts used hitherto for hydrosilylation are generally not satisfactory, particularly for the crosslinking of polysiloxanes by means of a hydrosilylation reaction.

Very active Ru catalysts for hydrosilylation, in particular for the crosslinking of polysiloxanes, have also been described in DE 102006017588 A1. However, these very active catalysts have the disadvantage of total or partial incompatibility with polysiloxanes and a hydrosilylation selectivity which is significantly below that of customary Pt hydrosilylation catalysts, for example the "Karstedt" catalyst. The compatibility with polysiloxanes can be increased, for example, by introduction of "silicophilic" ligands, as described, for example, in DE 102006017594 A1 by way of η$^6$-arene-Ru complexes. Despite the very good solubility of these catalysts in polysiloxanes, the activity and selectivity resulting from this class of catalyst in the crosslinking of polysiloxanes is still not always satisfactory.

SUMMARY OF THE INVENTION

It was therefore an object of the invention to provide a hydrosilylation catalyst which is soluble in polysiloxanes and is based on an Ru compound, and which does not have the disadvantages with respect to activity and selectivity of the Ru hydrosilylation catalysts described hitherto in the prior art and thus represents a genuine alternative to prior art Pt catalysts, particularly in the crosslinking of polysiloxanes. It has surprisingly been found that this these and other objects are achieved by uncharged Ru(0)-sulfoxide complex catalysts (D) of the general formula (I),

Formula (I)

characterized in that
at least one of the ligands L$^1$-L$^5$ is a sulfoxide ligand of the general formula (II)

Formula (II), where the radicals R$^1$ and R$^2$ are identical or different and are selected independently from the group consisting of
straight-chain and branched alkyl groups, alkenyl groups and alkynyl groups,
straight-chain and branched alkyl groups, alkenyl groups and alkynyl groups having at least one substituent selected from the group consisting of alkoxy, siloxy, aryloxy, aryl, silyl, alkoxycarbonyl, aryloxycarbonyl, acyloxy, carboxamido and carbamoyl groups and halogen atoms;
phenyl groups which are substituted or unsubstituted, where substituents are selected from the group consisting of alkyl, alkenyl, alkenyl, silyl, alkoxy, siloxy, aryloxy, aryl, alkoxycarbonyl, aryloxycarbonyl, acyloxy, carboxamido and carbamoyl groups and halogen atoms;

$R^1$ and $R^2$ are joined to form a heterocycle containing the sulfur atom or a heterocycle containing further heteroatoms, with the proviso that $R^1$ and $R^2$ together have 2-24 carbon atoms, and at least one of the ligands $L^1$-$L^5$ is a ligand which is π-bonded via one or two C=C functions and has the general formula (III)

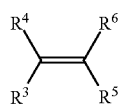

Formula (III)

where the radicals $R^3$-$R^6$ are identical or different and are selected independently from the group consisting of hydrogen, straight-chain or branched, cyclic or acyclic, $C_1$-$C_{50}$-alkyl, $C_2$-$C_{50}$-alkenyl, $C_2$-$C_{50}$-alkynyl, $C_6$-$C_{30}$-aryl radicals in which individual carbon atoms are unsubstituted or substituted by halogen, O, N, S, Si or P atoms, and the remaining ligands $L^1$-$L^5$ are identical or different and are selected from the group consisting of uncharged 2-, 4- or 6-electron donor ligands containing

CO;

CNR''', where R''' is selected from the group consisting of alkyl and aryl;

$PR'''_3$ and $P(OR''')_3$, where R''' is selected from the group consisting of alkyl and aryl;

ligands containing N donors, for example nitriles such as acetonitrile, benzonitrile or amines, pyridine;

ligands which contain S donors and do not correspond to the sulfoxides of the general formula (1), e.g. thioethers;

ligands containing O donors, for example linear or cyclic ethers such as dialkyl ethers or tetrahydrofuran, carbene ligands, for example N-heterocyclic carbenes, with the proviso that none of the ligands $L^1$-$L^5$ is 1,5-cyclooctadiene or 1,3,5-cyclooctatriene.

DETAILED DESCRIPTION OF THE PREFERRED EMBODIMENTS

The sulfoxide ligands can be bound to the ruthenium either via the sulfur atom or via the oxygen atom. Examples of sulfoxide ligands are dimethyl sulfoxide, diethyl sulfoxide, di-n-propyl sulfoxide, diisopropyl sulfoxide, di-n-butyl sulfoxide, di-tert-butyl sulfoxide, diallyl sulfoxide, methyl phenyl sulfoxide, etc. Examples of cyclic sulfoxide ligands are tetramethylene sulfoxide and 1,4-thioxane S-oxide. Dimethyl sulfoxide is particularly preferred as sulfoxide ligand.

When the ligand which is π-bonded via one or two C=C functions has more than one C=C function, chelate-like $\eta^4$-coordination can be present and two of the ligand coordination sites $L^1$-$L^5$ are occupied.

Examples of π-bonded ligands having one or more C=C functions are all acyclic olefins having two or more carbon atoms, e.g. ethene (for $R^3$-$R^6$=H), propene, all 1-olefins (for $R^3$-$R^5$=H, $R^6$=alkyl) such as 1-butene, 1-pentene, all 2-olefins.

Substituted olefins in which $R^3$-$R^6$ are identical or, independently of one another, hydrogen, halogen, nitro, nitrilo, hydroxy, alkoxy, aryloxy, amino, amido, etc.

Vinylsilanes and vinylsiloxanes such as 1,3-di-vinyl-1,1,3,3-tetramethyldisiloxane, vinyl-pentamethyldisiloxane, vinyltrimethylsilane.

Further examples of π-bonded ligands having one or more C=C functions are styrene, α-methylstyrene, indene, and cis- and trans-stilbene.

Examples of substituted π-bonded ligands having one or more C=C functions are allyl chloride, allyl bromide, allyl alcohol, allyl carbonate, allyl acetate, allyl glycidyl ether, allylbenzene, methallyl chloride, and crotyl chloride.

Furthermore, the C=C double bond in the π-bonded ligand can also be a constituent of a ring, so that $R^3$, $R^4$, $R^5$ and $R^6$ in pairs, singly or multiply, identical or different and independently of one another form a ring, resulting in cyclic, optionally substituted olefins having three or more carbon atoms, e.g. cyclopropene, cyclobutene, cyclopentene, cyclohexene, cycloheptene, cyclooctene, norbornene, etc.

An embodiment according to the invention of the Ru(0)-sulfoxide complex catalysts (D) in which only one ligand is a sulfoxide and only one ligand is a ligand which is π-bonded via only one C=C double bond is represented by the general formulae (IV) and (V),

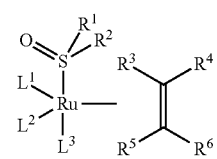

Formula (IV)

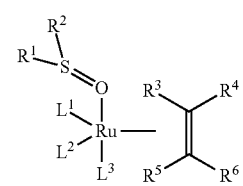

Formula (V)

where the radicals $R^4$ and $R^2$, $R^3$-$R^6$ and the ligands $L^1$-$L^3$ are as defined above.

The general formulae (VI) and (VII) show by way of example a further embodiment according to the invention of the Ru(0)-sulfoxide complex catalysts (D) in which only one ligand is a sulfoxide and one ligand is a ligand which is π-bonded via two C=C double bonds,

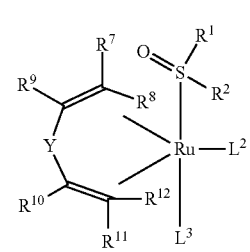

Formula (VI)

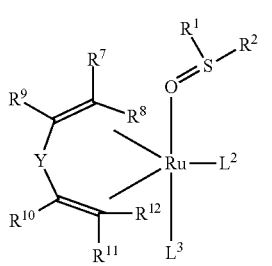

Formula (VII)

where the radicals $R^1$ and $R^2$ and the ligands $L^2$-$L^3$ are as defined above and $R^7$-$R^{12}$ in combination with the spacer Y are selected so that they correspond to the general formula (III).

π-bonded ligands which can be complexed to the ruthenium via two C=C functions are, for example, 1,3-butadiene, 2-methyl-1,3-butadiene (isoprene), 2,3-dimethyl-1,3-butadiene, 1,6-cyclodecene, norbornadiene, 1,2-divinylbenzene, 1,3-divinylbenzene, 1,4-divinylbenzene, diallyl phthalate, 1,3-divinyl-1,1,3,3-tetramethyldisiloxane, etc.

Particular preference is given to the coordination of 1,3-divinyl-1,1,3,3-tetramethyldisiloxane, as represented by the general formulae (VIII) and (IX),

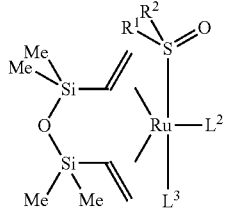

Formula (VIII)

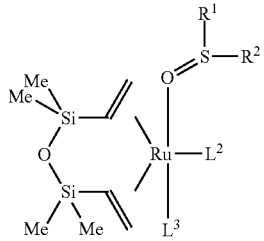

Formula (IX)

where the radicals $R^1$, $R^2$ and the ligands $L^2$ and $L^3$ are as defined above.

π-bonded ligands having two double bonds can also bond via only one double bond. In addition, π-bonded ligands having more than two double bonds can also bond via only one or two C=C functions to the ruthenium center, as, for example, in 1,3,5,7-tetravinyltetramethylcyclo-tetrasiloxane or diallyl maleate.

The coordination of π-bonded ligands via two C=C double bonds is preferred.

The synthesis of the Ru(0)-sulfoxide complex catalysts (D) of the invention can be carried out by the standard methods which are in principle known to those skilled in the art from the prior art.

A route via the readily available Ru(II) complex cis-RuCl$_2$(DMSO)$_4$, which can be obtained, for example, by a method analogous to that of Wilkinson et al., *J. Chem. Soc., Dalton Trans.* 1973, 204, has been found to be useful for the synthesis of the Ru(0) complexes (D) of the invention. The Ru(II) complex cis-RuCl$_2$(DMSO)$_4$ can, for example, be reacted with the C=C-functional ligand and a suitable reducing agent with elimination of DMSO and Cl$^-$ to form the corresponding Ru(0) complexes of the invention.

Suitable reducing agents are all reducing agents which are known from the prior art and are able to reduce Ru(II) to Ru(0). Particular mention may be made of alcohols such as methanol, ethanol, 1-propanol, 2-propanol, n-butanol, tert-butanol, etc. Mention may also be made of metallic reducing agents, in particular zinc and magnesium.

When an alcohol is used as reducing agent, it is advisable to use a base, e.g. Na$_2$CO$_3$, to scavenge the hydrogen chloride formed.

If a primary alcohol, e.g. ethanol, is used, carbon monoxide can be formed from the alcohol under particular reaction conditions and this carbon monoxide can be bound as ligand to the ruthenium.

A further possible way of carrying out the preparation is by reduction of other Ru(II)-halogen complexes or by reductions starting out from RuCl$_3$.

Furthermore, a preparation via a ligand exchange reaction on available Ru(0) complexes, for example Ru(COD)(COT), can also be carried out.

The following examples show some specific embodiments according to the invention of the Ru(0)-sulfoxide complex catalysts (D), but without restricting the invention to these.

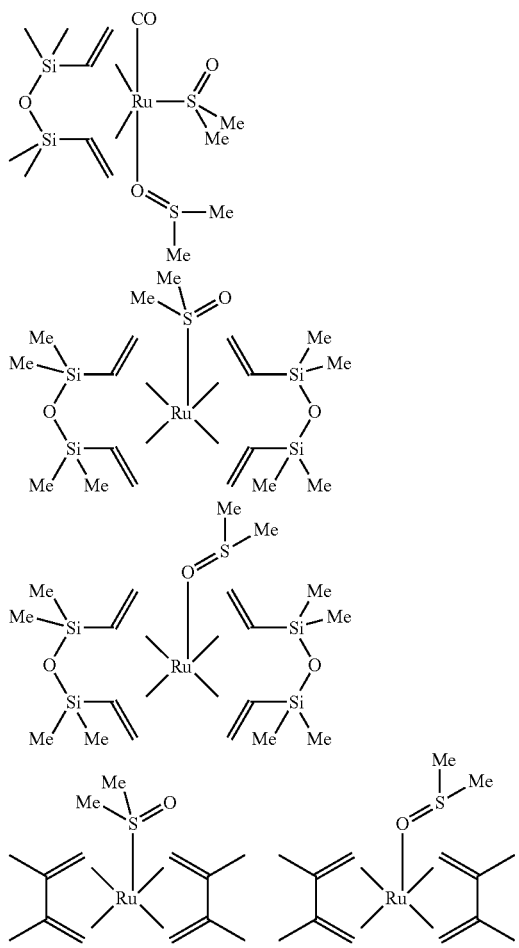

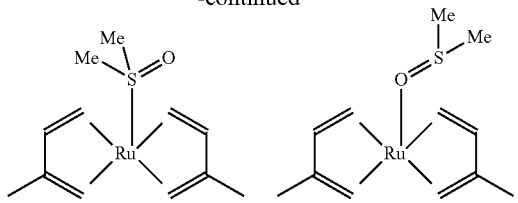

The Ru(0)-sulfoxide complex catalysts (D) of the invention are used for hydrosilylation reactions, for polymerization reactions, in which activation is effected by introduction of heat.

The inventive use of the Ru(0)-sulfoxide complex catalyst (D) can be effected generally in all hydrosilylation reactions, for example those which are known to those skilled in the art from the prior art and are described, for example, in Walter Noll "Chemie and Technologie der Silicone", Verlag Chemie GmbH, Weinheim/Bergstr. 1968; Bogdan Marciniec, "Comprehensive Handbook on Hydrosilylation", Oxford: Pergamon Press, 1992 and the complex catalyst (D) can be used generally in all hydrosilylatable, in particular crosslinkable, compositions.

The invention further provides hydrosilylatable compositions containing
(A) a compound having at least one aliphatic unsaturated carbon-carbon bond,
(B) a compound having at least one silicon-hydrogen bond and
(D) at least one Ru(0)-sulfoxide complex catalyst according to the invention as described above.

The hydrosilylatable compositions of the invention preferably contain compounds which have at least one aliphatically unsaturated carbon-carbon bond and are selected from the group of vinyl-functional organosilanes and vinyl-terminated polydimethylsiloxanes and compounds which have at least one silicon-hydrogen bond and are selected from the group of SiH-functional polysiloxanes and Si—H-functional organosilanes.

In a preferred embodiment, hydrosilylatable compositions are, in particular, crosslinkable compositions.

The compounds and amounts of (A) and (B) which are useful are adequately known from the prior art.

In a preferred embodiment of the hydrosilylatable compositions, the compositions are addition-crosslinking compositions containing
(i) at least one compound selected from the group consisting of the compounds (A'), (B') and (C),
  where
  (A') is an organic compound and/or an organosilicon compound containing at least two radicals having aliphatic carbon-carbon multiple bonds,
  (B') an organosilicon compound containing at least two Si-bonded hydrogen atoms and
  (C) an organosilicon compound containing SiC-bonded radicals having aliphatic carbon-carbon multiple bonds and Si-bonded hydrogen atoms,
  with the proviso that the composition contains at least one compound having aliphatic carbon-carbon multiple bonds and at least one compound having Si-bonded hydrogen atoms,
  and
(ii) at least one Ru(0)-sulfoxide complex catalyst (D) according to the invention as described above.

The compounds and amounts of (A'), (B') and (C) are adequately known from the prior art.

Preference is given to using compounds of the general formulae (VI) to (IX) as Ru(0)-sulfoxide complex catalyst (D) in the hydrosilylatable compositions of the invention. Particular preference is given to using the further specific examples of (D) given above in the compositions.

The process of the invention for hydrosilylating the compositions is carried out with introduction of energy, preferably by introduction of heat.

Examples of the compounds (A) and (A') are vinyl-functional organosilanes and vinyl-terminated poly-dimethylsiloxanes.

Examples of compounds (B) and (B') are SiH-functional polysiloxanes and Si—H-functional organosilanes.

The Ru(0)-sulfoxide complex catalysts (D) of the invention are generally used in the compositions in such an amount that an Ru content of 5-1000 ppm, preferably 5-500 ppm, based on the total mass of the composition, is obtained.

The hydrosilylation reactions are generally carried out at temperatures in the range from room temperature, in particular 20° C., to 200° C., preferably in the range from 50° C. to 160° C., and a pressure of from 900 to 1100 hPa. However, it is also possible to employ higher or lower temperatures and pressures.

The hydrosilylation reactions can be carried out either in air or under an inert gas atmosphere (nitrogen, argon); the reaction is preferably carried out under an inert gas atmosphere.

In particular, such hydrosilylation reactions in which C=C-functional polysiloxanes are reacted with SiH-functional polysiloxanes or C=C functional organo-silanes are reacted with SiH-functional organosilanes are catalyzed.

Particular preference is given to the reaction of vinyl-terminated polydimethylsiloxanes (A') with SiH-functional polysiloxanes (B') of the general formula (X)

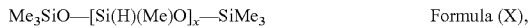

Me$_3$SiO—[Si(H)(Me)O]$_x$—SiMe$_3$   Formula (X), where
x is from 1 to 500, preferably from 1 to 100,
and that of Si-vinyl-functional organosilanes (A') with Si—H-functional organosilanes (B').

Examples of hydrosilylatable Si-vinyl-functional organosilanes (A) are vinyltrimethylsilane, vinyltriethoxysilane, vinylmethyldiethoxysilane, vinylmethyldimethoxysilane, and vinyltrichlorosilane.

As specific examples of SiH-functional organosilanes (B), mention may be made of HSi(OR')$_3$, where R' is an alkyl radical, HSi(Me)$_{3-o}$Cl$_o$, where o is from 1 to 3 and HSiR"$_3$, where R" is an alkyl or aryl radical.

The invention further provides silicone elastomers which can be obtained by crosslinking the above-described addition-crosslinking compositions.

The compositions of the invention can be one-component silicone compositions or two-component silicone compositions. In the latter case, the two components of the compositions of the invention can contain all constituents in any combination, generally with the proviso that one component does not at the same time contain siloxanes having an aliphatic multiple bond, siloxanes having Si-bonded hydrogen and catalyst, i.e. essentially not at the same time the constituents (A), (B) and (D) or (C) and (D) or (A'), (B') and (D). However, the compositions of the invention are preferably one-component compositions.

The invention likewise provides coatings, in particular antiadhesive coatings, for example for producing release, covering and interleaving papers, which can be obtained by crosslinking the above-described hydro-silylatable compositions according to the invention, in particular the polyorganosiloxane compositions described.

The invention likewise provides polysiloxane or organosilane compositions prepared by the process of the invention, which can be used, for example, for producing dental impressions, adhesives, release liners, flat seals, sealants and coatings.

The compounds (A) and (B) or (A') and (B') and (C) used in the compositions of the invention are, as is known, selected so that crosslinking is possible. Thus, for example, compound (A) has at least two aliphatically unsaturated radicals and siloxane (B) has at least three Si-bonded hydrogen atoms, or compound (A) has at least three aliphatically unsaturated radicals and siloxane (B) has at least two Si-bonded hydrogen atoms, or else siloxane (C) which has aliphatically unsaturated radicals and Si-bonded hydrogen atoms in the abovementioned ratios is used instead of compounds (A') and (B').

Examples of organic compounds (A') are 1,3,5-trivinyl cyclohexane, 2,3-dimethyl-1,3-butadiene, 7-methyl-3-methylene-1,6-octadiene, 2-methyl-1,3-butadiene, 1,5-hexadiene, 1,7-octadiene, 4,7-methylene-4,7,8,9-tetrahydroindene, methylcyclopentadiene, 5-vinyl-2-norbornene, bicyclo[2.2.1]hepta-2,5-diene, 1,3-diisopropenylbenzene, polybutadiene containing vinyl groups, 1,4-divinylcyclohexane, 1,3,5-triallylbenzene, 1,3,5-trivinylbenzene, 1,2,4-trivinylcyclohexane, 1,3,5-tri-isopropenylbenzene, 1,4-divinylbenzene, 3-methyl-1,5-heptadiene, 3-phenyl-1,5-hexadiene, 3-vinyl-1,5-hexa-diene and 4,5-dimethyl-4,5-diethyl-1,7-octadiene, N,N'-methylenebis(acrylamide), 1,1,1-tris-(hydroxymethyl)propane triacrylate, 1,1,1-tris-(hydroxymethyl)propane trimethacrylate, tripropylene glycol diacrylate, diallyl ether, diallylamine, diallyl carbonate, N,N'-diallylurea, triallylamine, tris(2-methylallyl)amine, 2,4,6-triallyloxy-1,3,5-triazine, triallyl-s-triazine-2,4,6(1H,3H,5H)trione, diallyl malonate, polyethylene glycol diacrylate, polyethylene glycol dimethacrylate, poly(propylene glycol) methacrylate.

However, the silicone compositions of the invention preferably contain an aliphatically unsaturated organosilicon compound as constituent (A'), with it being possible to use all aliphatically unsaturated organosilicon compounds which are useful in addition-crosslinking compositions, and also, for example, silicone block copolymers having urea segments, silicone block copolymers having amide segments and/or imide segments and/or ester-amide segments and/or polystyrene segments and/or silarylene segments and/or carborane segments and silicone graft copolymers having ether groups.

As organosilicon compounds (A') containing SiC-bonded radicals having aliphatic carbon-carbon multiple bonds, preference is given to using linear or branched poly-organosiloxanes composed of units of the average general formula (XI)

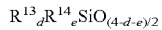      Formula (XI)

where
the radicals $R^{13}$ can be identical or different and are each an organic or inorganic radical which is free of aliphatic carbon-carbon multiple bonds,
the radicals $R^{14}$ can be identical or different and are each a monovalent, substituted or unsubstituted, SiC-bonded hydrocarbon radical having an aliphatic carbon-carbon multiple bond,
d is 0, 1, 2 or 3 and
e is 0, 1 or 2,
with the proviso that the sum d+e is less than or equal to 3 and on average at least 2 radicals $R^{14}$ are present per molecule.

The radical $R^{13}$ in the general formula (XI) can be a monovalent or polyvalent radical, with the polyvalent radicals, e.g. bivalent, trivalent and tetravalent radicals, then joining a plurality of, for example two, three or four, siloxy units of the general formula (XI) to one another.

Further examples of $R^{13}$ are the monovalent radicals —F, —Cl, —Br, $OR^5$, —CN, —SCN, —NCO and SiC-bonded, substituted or unsubstituted hydrocarbon radicals which may be interrupted by oxygen atoms or the group —C(O)—, and also divalent radicals of the formula (XI) which are Si-bonded at both ends, where $R^5$ is as defined above. If the radical $R^{13}$ is an SiC-bonded, substituted hydrocarbon radical, preferred substituents are halogen atoms, phosphorus-containing radicals, cyano radicals, —$OR^x$, —$NR^x$—, —$NR^x_2$, —$NR^x$—C(O)—$NR^x_2$, —C(O)—$NR^x_2$, —C(O)$R^x$, —C(O)$OR^x$, —$SO_2$-Ph and —$C_6F_5$. Here, the radicals Rx are identical or different and are each, independently of one another, a hydrogen atom or a monovalent hydrocarbon radical having from 1 to 20 carbon atoms and Ph is the phenyl radical.

Examples of radicals $R^{13}$ are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals, hexyl radicals such as the n-hexyl radical, heptyl radicals such as the n-heptyl radical, octyl radicals such as the n-octyl radical and isooctyl radicals such as the 2,2,4-trimethylpentyl radical, nonyl radicals such as the n-nonyl radical, decyl radicals such as the n-decyl radical, cycloalkyl radicals such as cyclopropyl, cyclopentyl, cyclohexyl, cycloheptyl radicals and methylcyclohexyl radicals, unsaturated radicals such as the allyl, 5-hexenyl, 7-octenyl, cyclohexenyl and styryl radicals, aryl radicals such as phenyl radicals, o-, m-, p-tolyl radicals, xylyl radicals and ethylphenyl radicals, and aralkyl radicals such as the benzyl radical and the α- and β-phenylethyl radicals.

Examples of substituted radicals $R^{13}$ are haloalkyl radicals such as the 3,3,3-trifluoro-n-propyl radical, the 2,2,2,2',2',2'-hexafluoroisopropyl radical, the heptafluoroisopropyl radical, haloaryl radicals such as the o-, m- and p-chlorophenyl radicals, —$(CH_2)_r$—$N(R^x)C(O)NR^x_2$, —$(CH_2)_r$—C(O)$NR^x_2$, —$(CH_2)_r$—C(O)$R^x$, —$(CH_2)_r$—C(O)$OR^x$, —$(CH_2)_r$—C(O)$NR^x_2$, —$(CH_2)_r$—C(O)HCH$_2)_s$—C(O)CH$_3$, —$(CH_2)_r$—$NR^x$—$(CH_2)_s$—$NR^x_2$, —$(CH_2)_r$—O—CO—Rx, —$(CH_2)_r$—O—$(CH_2)_s$—CH(OH)—CH$_2$OH, —$(CH_2)_r$—$(OCH_2CH_2)_s$—$OR^x$, —$(CH_2)_r$—$SO_2$-Ph and —$(CH_2)_r$—O—$C_6F_5$, where $R^x$ is as defined above, r and s are identical or different and are each integers in the range from 0 to 10 and Ph is the phenyl radical.

Examples of divalent radicals $R^{13}$ which are Si-bonded at both ends as per the general formula (XI) are radicals derived from the monovalent examples given above for radical $R^{13}$ by an additional bond being formed by replacement of a hydrogen atom. Examples of such radicals are —$(CH_2)_r$—, —CH(CH$_3$)—, —C(CH$_3$)$_2$—, —CH(CH$_3$)—CH$_2$—, —$C_6H_4$—, —CH(Ph)—CH$_2$—, —C(CF$_3$)$_2$—, —$(CH_2)_n$—$C_6H_4$—$(CH_2)_r$—, —$(CH_2)_r$—$C_6H_4$—$C_6H_4$—$(CH_2)_r$—, —$(CH_2O)_s$—, —$(CH_2CH_2O)_s$—, —$(CH_2)_r$—$O_t$—$C_6H_4$—$SO_2$—$C_6H_4$—$O_t$—$(CH_2)_n$— where t is 0 or 1, r and s are as defined above and Ph is the phenyl radical.

The radical $R^{13}$ is preferably a monovalent, SiC-bonded, substituted or unsubstituted hydrocarbon radical which has from 1 to 18 carbon atoms and is free of aliphatic carbon-carbon multiple bonds, more preferably a monovalent, SiC-bonded hydrocarbon radical which has from 1 to 6 carbon atoms and is free of aliphatic carbon-carbon multiple bonds, and in particular the methyl or phenyl radical.

The radical $R^{14}$ can be any group which can undergo an addition reaction (hydrosilylation) with an SiH-functional compound.

If the radical $R^{14}$ is an SiC-bonded, substituted hydrocarbon radical, preferred substituents are halogen atoms, cyano radicals and —$OR^x$, where $R^x$ is as defined above.

The radical $R^{14}$ is preferably an alkenyl or alkynyl group having from 2 to 16 carbon atoms, e.g. vinyl, allyl, methallyl, 1-propenyl, 5-hexenyl, ethynyl, butadienyl, hexadienyl, cyclopentenyl, cyclopenta-dienyl, cyclohexenyl, vinylcyclohexylethyl, divinyl-cyclohexylethyl, norbornenyl, vinylphenyl and styrene radicals, with particular preference being given to using vinyl, allyl and hexenyl radicals.

The molecular weight of the constituent (A') can vary within wide limits, for example from $10^2$ to $10^6$ g/mol. Thus, the constituent (A') can be, for example, a relatively low molecular weight alkenyl-functional oligosiloxane such as 1,3-divinyltetramethyldisiloxane, or else a highly polymeric polydimethylsiloxane having Si-bonded vinyl groups along the chain or at the end of the chain e.g. having a molecular weight of $10^5$ g/mol (number average determined by means of NMR). The structure of the molecules forming the constituent (A') is also not fixed; in particular, the structure of a relatively high molecular weight, i.e. oligomeric or polymeric, siloxane can be linear, cyclic, branched or resin-like, network-like. Linear and cyclic polysiloxanes are preferably composed of units of the formulae $R^{13}_3SiO_{1/2}$, $R^{14}R^{13}_2SiO_{1/2}$, $R^{14}R^{13}SiO_{2/2}$ and $R^{13}_2SiO_{2/2}$, where $R^{13}$ and $R^{14}$ are as defined above. Branched and network-like polysiloxanes additionally contain trifunctional and/or tetrafunctional units, with preference being given to those of the formulae $R^{13}SiO_{3/2}$, $R^{14}SiO_{3/2}$ and $SiO_{4/2}$. Of course, it is also possible to use mixtures of different siloxanes which satisfy the criteria of the constituent (A').

Particular preference is given to using vinyl-functional, essentially linear polydiorganosiloxanes having a viscosity of from 0.01 to 500,000 Pa·s, particularly more preferably from 0.1 to 100,000 Pa·s, in each case at 25° C., as component (A').

As organosilicon compound (B'), it is possible to use all hydrogen-functional organosilicon compounds which have also been used hitherto in addition-crosslinkable compositions.

As organopolysiloxanes (B') which have Si-bonded hydrogen atoms, preference is given to using linear, cyclic or branched organopolysiloxanes composed of units of the average general formula (XII)

$$R^{13}_fH_gSiO_{(4-f-g)/2}$$ <span>Formula (XII)</span> where
the radicals $R^{13}$ can be identical or different and are as defined above,
f is 0, 1, 2 or 3 and
g is 0, 1 or 2,
with the proviso that the sum of f+g is less than or equal to 3 and on average at least two Si-bonded hydrogen atoms are present per molecule.

The organopolysiloxane (B') used according to the invention preferably contains Si-bonded hydrogen in the range from 0.04 to 1.7 percent by weight, based on the total weight of the organopolysiloxane (B').

The molecular weight of the constituent (B') can likewise vary within wide limits, for instance from $10^2$ to $10^6$ g/mol. Thus, the constituent (B') can be, for example, a relatively low molecular weight SiH-functional oligosiloxane such as tetramethyldisiloxane but can also be a highly polymeric polydimethylsiloxane having SiH groups in the chain or at the end of the chain or a silicone resin having SiH groups. The structure of the molecules forming the constituent (B') is also not fixed; in particular, the structure of a relatively high molecular weight, i.e. oligomeric or polymeric, SiH-containing siloxane can be linear, cyclic, branched or resin-like, network-like. Linear and cyclic polysiloxanes are preferably composed of units of the formulae $R^{13}_3SiO_{1/2}$, $HR^{13}_2SiO_{1/2}$, $HR^{13}SiO_{2/2}$ and $R^{13}_2SiO_{2/2}$, where $R^{13}$ is as defined above. Branched and network-like polysiloxanes additionally contain trifunctional and/or tetrafunctional units, with preference being given to those of the formulae $R^{13}SiO_{3/2}$, $HSiO_{3/2}$ and $SiO_{4/2}$. Of course, it is also possible to use mixtures of different siloxanes which satisfy the criteria of the constituent (B'). In particular, the molecules forming the constituent (B) may optionally also contain aliphatically unsaturated groups in addition to the obligatory SiH groups. Particular preference is given to using low molecular weight SiH-functional compounds such as tetrakis(dimethylsiloxy)silane and tetramethylcyclotetrasiloxane and also relatively high molecular weight, SiH-containing siloxanes such as poly(hydrogenmethyl)-siloxane and poly(dimethylhydrogenmethyl)siloxane having a viscosity at 25° C. of from 10 to 10,000 mPa·s, or analogous SiH-containing compounds in which part of the methyl groups may have been replaced by 3,3,3-trifluoropropyl or phenyl groups.

Constituent (B') is preferably present in the crosslinkable silicone total compositions of the invention in such amounts that the molar ratio of SiH groups to aliphatically unsaturated groups is from 0.1 to 20, more preferably from 1.0 to 5.0.

The components (A') and (B') of invention are commercial products or can be prepared by methods customary in chemistry.

Instead of components (A') and (B'), the compositions of the invention can contain organopolysiloxanes (C) which have aliphatic carbon-carbon multiple bonds and Si-bonded hydrogen atoms. It is also possible for the silicone compositions of the invention to contain all three components (A'), (B') and (C).

If siloxanes (C) are used, these are preferably siloxanes composed of units of the formulae (XIII) to (XV)

$$R^{13}_kSiO_{4-k/2},$$ <span>Formula (XIII)</span>

$$R^{13}_hR^{14}SiO_{3-h/2}$$ <span>Formula (XIV)</span>

$$R^{13}_iHSiO_{3-i/2}$$ <span>Formula (XV)</span> where
$R^{13}$ and $R^{14}$ are as defined above,
k is 0, 1, 2 or 3,
h is 0, 1 or 2 and
i is 0, 1 or 2,
with the proviso that at least 2 radicals $R^{14}$ and at least 2 Si-bonded hydrogen atoms are present per molecule.

Examples of organopolysiloxanes (C) are organo-polysiloxanes composed of $SiO_{4/2}$, $R^{13}_3SiO_{1/2}$, $R^{13}_2R^{14}SiO_{1/2}$ and $R^{13}_2HSiO_{1/2}$ units, known as MQ resins, where these resins can additionally contain $R^{13}SiO_{3/2}$ and $R^{13}_2SiO$ units, and also linear organopolysiloxanes consisting essentially of $R^{13}_2R^{14}SiO_{1/2}$, $R^{13}_2SiO$ and $R^{13}HSiO$ units, where $R^{13}$ and $R^{14}$ are as defined above.

The organopolysiloxanes (C) preferably have an average viscosity of from 0.01 to 500,000 Pa·s, particularly more preferably from 0.1 to 100,000 Pa·s, in each case at 25° C. Organopolysiloxanes (C) can be prepared by methods customary in chemistry.

Apart from the components (A'), (B'), (C) and (D), the curable compositions of the invention can also contain all further materials which are useful for producing addition-crosslinkable compositions.

Examples of reinforcing fillers which can be used as component (E) in the compositions of the invention are pyrogenic or precipitated silicas having BET surface areas of at least 50 m²/g and also carbon blacks and activated carbons such as furnace black and acetylene black, with preference being given to pyrogenic and precipitated silicas having BET surface areas of at least 50 m²/g.

The silica fillers mentioned above can have hydrophilic character or can have been hydrophobicized by known methods. When hydrophilic fillers are mixed in, the addition of a hydrophobicizing agent is necessary.

The amount of actively reinforcing filler (E) present in the crosslinkable composition of the invention is in the range from 0 to 70% by weight, preferably from 0 to 50% by weight.

The compositions of the invention, in particular the polyorganosiloxane compositions, can, if desired, contain further additives as constituent (F) in a proportion of up to 70% by weight, preferably from 0.0001 to 40% by weight. These additives are, for example, inactive fillers, resin-like polyorgano-siloxanes which are different from the siloxanes (A), (B), (A'), (B') and (C), inhibitors, stabilizers, dispersants, solvents, bonding agents, pigments, dyes, plasticizers, organic polymers, heat stabilizers, fungicides, fragrances, rheological additives, corrosion inhibitors, oxidation inhibitors, light stabilizers, flame retardants and agents for influencing the electrical properties, etc. These include additives such as quartz flour, diatomaceous earth, clays, chalk, lithophones, carbon blacks, graphite, metal oxides, metal carbonates, metal sulfates, metal salts of carboxylic acids, metal dusts, fibers such as glass fibers, polymer fibers, polymer powders, dyes, pigments, etc.

The compositions of the invention can, if necessary, be dissolved, dispersed, suspended or emulsified in liquids. The compositions of the invention can, in particular depending on the viscosity of the constituents and the filler content, have a low viscosity and be pourable, have a paste-like consistency, be pulverulent or can be malleable, high-viscosity compositions, which can be the case for compositions frequently referred to in the art as RTV-1, RTV-2, LSR and HTV. In particular, the compositions of the invention can, if they are highly viscous, be converted into the form of granules. Here, the individual granule can contain all components or the components used according to the invention are incorporated separated into different individual granules. The elastomeric properties of the crosslinked silicone compositions of the invention likewise encompass the entire range from extremely soft silicone gels through rubber-like materials to highly crosslinked silicones having glass-like behavior.

The compositions of the invention can be produced by known methods, for example by homogeneous mixing of the individual components. The order can be any desired order, but preference is given to homogeneously mixing the ruthenium catalyst (D) with a mixture of (A'), (B') and optionally (E) and (F). The ruthenium catalyst (D) used according to the invention can be incorporated as solid or as solution in a desired solvent or as masterbatch, homogeneously mixed with a small amount of (A'). Mixing is carried out as a function of the viscosity of (A), for example by means of a stirrer, in a high-speed stirrer, on rollers or in a kneader.

The components (A') to (F) used according to the invention can in each case be a single type of such a component or a mixture of at least two different types of such a component.

The present invention further provides moldings produced by crosslinking the compositions of the invention.

The silicone compositions of the invention and the crosslinked products produced therefrom can be used for all purposes for which elastomers or organopolysiloxane compositions which can be crosslinked to form elastomers are useful. These encompass, for example, silicone coating or impregnation of any substrates, the production of moldings, for example by injection molding, vacuum extrusion, extrusion, casting in a mold and compression molding, and impressions, use as sealants, embedding compositions and potting compounds, etc.

The use of the compounds of the invention as catalysts in hydrosilylation results, in particular, in the hydrosilylation selectivity being very high and the compatibility with polysiloxanes being very good, which at the same time also leads to a very high activity.

The crosslinkable silicone compositions of the invention have the advantage that they can be produced in a simple process using readily available starting materials and thus economically. The crosslinkable compositions of the invention have the further advantage that as one-component formulation they have a good storage stability at 25° C. and ambient pressure and crosslink quickly only at elevated temperature. The silicone compositions of the invention have the advantage that in the case of a two-component formulation they give, after mixing of the two components, a crosslinkable silicone composition whose processibility is retained over a long period of time at 25° C. and ambient pressure, i.e. displays an extremely long pot life, and crosslinks quickly only at elevated temperature. The compositions of the invention have the further advantage that the hydrosilylation reaction does not slow as the reaction time increases.

The following examples serve to illustrate the invention and are not to be construed as any form of restriction.

All parts and percentages reported are, unless indicated otherwise, by weight. In the following, all viscosities reported are based on a temperature of 25° C.

EXAMPLES

Preparation of the Catalysts

Example 1

Synthesis of Ru(CO)(k-O-DMSO)(k-S-DMSO) ($\eta^4$-Vi$_2$Me$_4$Si$_2$O)

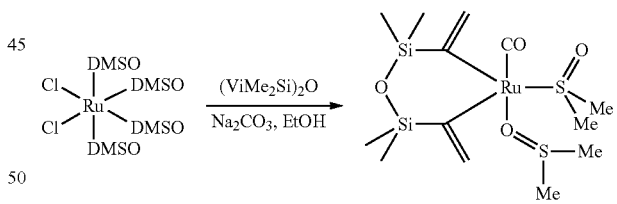

In an argon atmosphere, a mixture of 2.32 g (4.78 mmol) of cis-RuCl$_2$(DMSO)$_4$, 1.42 g of Na$_2$CO$_3$ (13.4 mmol) and 11.5 ml of divinyltetramethyldisiloxane (=(ViMe$_2$Si)$_2$O) is heated in 85 ml of absolute ethanol under reflux for 12 hours, forming a yellow-orange suspension. After cooling to room temperature, all volatile constituents are taken off under reduced pressure. The remaining oily residue is extracted four times with 25 ml each time of heptane at 40° C. for 30 minutes and filtered through a preheated frit. The combined extracts are evaporated under reduced pressure. This leaves a beige, waxy solid with a proportion of brown oil. The solid is partly crystalline. An X-ray structure analysis could be carried out on a corresponding single crystal.

The crude product is admixed with 2 ml of pentane and stored at −20° C. for a number of hours. The supernatant solution is separated off cold and the solid is dried under reduced pressure after warming to room temperature.

Yield: 1.35 g (51%).

$^1$H-NMR (300 MHz, $C_6D_6$): δ=2.96 (d, J=11.4 Hz, 2H, $CH_2$=CH, 2.81 (d, J=13.4 Hz, 2H, $CH_2$=CH, 2.80 [s, 6H, $(CH_3)_2S$=O, Ru—S], 1.79 [dd, J=13.4 Hz, J=11.4 Hz, 2H, $CH_2$=CH—Si], 1.41 [s, 6H, $(CH_3)_2S$=O, Ru—O] 0.72 [s, 6H, $(CH_3)_2Si$], 0.41 ppm [s, 6H, $(CH_3)_2Si$].

$^{13}C\{^1H\}$-NMR (125.8 MHz, $C_6D_6$): δ=202.43 (s, CO), 50.46, 47.58, 43.25, 38.92 [4s, $CH_2$=CH—Si+$(CH_3)_2S$=O] 3.47 ($CH_3Si$), −0.98 ppm ($CH_3Si$).

$^{29}Si\{^1H\}$-NMR (99.4 MHz, $C_6D_6$): δ=1.60 ppm (s).

IR: 1896, 1885 cm$^{-1}$ (vs, CO).

Example 2

Synthesis of Ru(η$^4$-dmbtd)$_2$(k-S-DMSO)

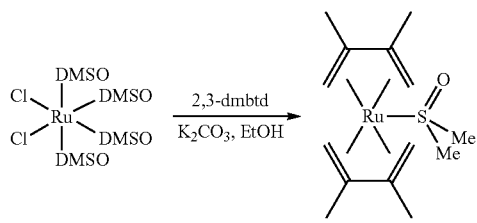

In an argon atmosphere, a mixture of 4.03 g (8.32 mmol) of cis-RuCl$_2$(DMSO)$_4$, 6.83 g (83.2 mmol) of 2,3-dimethylbutadiene (=2,3 dmbtd) and 11.51 g (83.2 mmol) of anhydrous $K_2CO_3$ together with 200 ml of absolute ethanol are placed in a reaction vessel and heated under reflux for 12 hours. Volatiles are removed under reduced pressure and the residue is extracted with about 150 ml of $CH_2Cl_2$. The extract is evaporated under reduced pressure and the residue is extracted with about 250 ml of pentane. The extract is evaporated under reduced pressure to a volume of about 30 ml and stored overnight at −80° C. The supernatant solution is separated off cold and the residue is dried under reduced pressure. Yield: 1.53 g (54%).

$^1$H-NMR ($C_6D_6$): δ=2.75 [s, 6H, $(CH_3)_2S$=O], 1.96 [s, 4H, $CH_2$=C(Me) $H_{exo}$], 1.49 (s, 12H, $CH_3C$=$CH_2$), 0.16 ppm [s, 4H, $CH_2$=C(Me), $H_{endo}$].

$^{13}C\{^1H\}$-NMR ($C_6D_6$): δ=93.3 [s, C(Me)=$CH_2$, $C_{quart}$], 49.7 [s, $(CH_3)_2S$=O], 42.4 [s, $CH_2$=C(Me)], 18.3 ppm (s, $CH_3$—C=$CH_2$).

Examination of the Catalytic Properties

Examples 3 & 4 and Comparative Example 1

A mixture of 2.5 g (about 2.63 mmol) of H-polymer 13 and 1.44 g (5.78 mmol) of 3-vinylheptamethyltrisiloxane is admixed with an appropriate amount of a catalyst (300 ppm of Ru or 100 ppm of Pt based on the total mass of the batch) and stirred at 120° C. for 15 minutes. Analysis of the hydrosilylation reaction (starting material conversion, selectivity to the β-addition product of the hydrosilylation, yield) is carried out by $^1$H-NMR. The results are shown in Table 1.

TABLE 1

| Example | Catalyst | Conversion [%] | Selectivity [%] | Yield [%] |
|---|---|---|---|---|
| 3 | Ru catalyst from Example 1 | 98 | 93 | 92 |
| 4 | Ru catalyst from Example 2 | 97 | 81 | 78 |
| Comparative example 1 | Pt-divinyltetramethyl-disiloxane complex ("Karstedt catalyst"), in xylene | 100 | 91 | 91 |

Examples 5 & 6 and Comparative Example 2

10.0 g of a vinyldimethylsiloxy-terminated poly-dimethylsiloxane having a viscosity of 500 mPa·s are admixed with an appropriate amount of a catalyst (300 ppm of Ru or 100 ppm of Pt based on the total mass of the batch), mixed intensively in a round-bottom flask and admixed with 250 mg of an SiH-functional polysiloxane of the formula Me$_3$SiO—[Si(H)Me—O]$_{48}$—SiMe$_3$ and once again mixed intensively. The mixture is stirred at 160° C. on a preheated oil bath. The time until the gelling process has progressed to such a degree that stirring by means of a magnetic stirrer bar at 250 rpm is no longer possible is determined. The hardness of the polymer is determined by visual assessment. The results are shown in Table 2.

TABLE 2

| Example | Catalyst | Crosslinking time | Hardness of the polymer |
|---|---|---|---|
| 5 | Ru catalyst from Example 1 | 54 s | Hard, brittle polymer |
| 6 | Ru catalyst from Example 2 | 41 s | Hard, brittle polymer, somewhat softer than in Example 5 |
| Comparative example 2 | Pt-divinyltetramethyl-disiloxane complex ("Karstedt catalyst"), in xylene | <5 s | Very hard and brittle polymer |

Example 7 and Comparative Example 3

50.0 g of a vinyldimethylsiloxy-terminated poly-dimethylsiloxane having a viscosity of 20 Pa·s and 1.0 g of SiH crosslinker are homogeneously mixed by means of a model RE 162 stirrer from Janke & Kunkel IKA-Labortechnik; the SiH crosslinker is a copolymer composed of dimethylsiloxy, methylhydrogensiloxy and trimethylsiloxy units and having a viscosity of 330 mPa·s and a content of Si-bonded hydrogen of 0.46% by weight. The appropriate amount of a catalyst (10 ppm of Ru or Pt based on the total mass of the batch) is subsequently dissolved in 0.5 ml of dichloromethane, added and stirred in at room temperature.

The start temperatures are determined at 50° C. using a method based on DIN53529T3. These are dependent on the method parameters selected.

The pot lives are determined by visual assessment of a low-viscosity model formulation. The results are shown in Table 3.

TABLE 3

| Example | Catalyst | Start temperature | Pot life at 50° C. |
|---|---|---|---|
| 7 | Ru catalyst from Example 1 | 119° C. | 10 d |
| Comparative example 3 | Pt-divinyltetramethyl-disiloxane complex ("Karstedt catalyst") + inhibitor (ECH) | 103° C. | <1 d |

The Ru catalyst of the invention displays a good activity with a sufficiently long pot life of 10 d (=days). In contrast, the platinum catalyst has a short pot life at 50° C. of less than 1 day despite addition of the inhibitor 1-ethynyl-1-cyclohexanol (ECH).

The invention claimed is:

1. A composition comprising a Ru(0)-sulfoxide complex catalyst (D) of the formula (I),

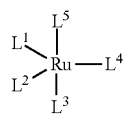
(I)

wherein
a) at least one of the ligands $L^1$-$L^5$ is a sulfoxide ligand of the formula (II)

$$R^1—S(=O)—R^2 \quad (II),$$

where the radicals $R^1$ and $R^2$ are identical or different and are selected independently from the group consisting of straight-chain and branched alkyl groups, alkenyl groups and alkynyl groups; straight-chain and branched alkyl groups, alkenyl groups and alkynyl groups having at least one substituent selected from the group consisting of alkoxy, siloxy, aryloxy, aryl, silyl, alkoxycarbonyl, aryloxycarbonyl, acyloxy, carboxamido, carbamoyl groups and halogen atoms; and phenyl groups which are substituted or unsubstituted, where substituents are selected from the group consisting of alkyl, alkenyl, alkynyl, silyl, alkoxy, siloxy, aryloxy, aryl, alkoxycarbonyl, aryloxycarbonyl, acyloxy, carboxamido and carbamoyl groups and halogen atoms;
and wherein $R^1$ and $R^2$ are optionally joined to form a heterocycle containing the sulfur atom or a heterocycle containing further heteroatoms,
with the proviso that $R^1$ and $R^2$ together have 2-24 carbon atoms;
b) at least one of the ligands $L^1$-$L^5$ is a ligand which is π-bonded via one or two C=C functions and has the formula (III)

(III)

where
the radicals $R^3$-$R^6$ are selected independently from the group consisting of hydrogen, straight-chain or branched, cyclic or acyclic, $C_1$-$C_{50}$-alkyl, $C_2$-$C_{50}$-alkenyl, $C_2$-$C_{50}$-alkynyl, and $C_6$-$C_{30}$-aryl radicals in which individual carbon atoms are unsubstituted or substituted by halogen, O, N, S, Si or P atoms, and
c) remaining ligands $L^1$-$L^5$ are identical or different and are selected from the group consisting of uncharged 2-, 4- or 6-electron donor ligands containing CO; CNR'", where R'" is selected from the group consisting of alkyl and aryl; PR'"$_3$ and P(OR'")$_3$, where R'" is selected from the group consisting of alkyl and aryl; ligands containing N donors; ligands which contain S donors and do not correspond to the sulfoxides of formula (I); ligands containing O donors; and carbene ligands;
with the proviso that none of the ligands $L^1$-$L^5$ is 1,5-cyclooctadiene or 1,3,5-cyclooctatriene.

2. The composition of claim 1 which is a hydrosilylatable composition comprising
(A) at least one compound having at least one aliphatic unsaturated carbon-carbon bond,
(B) at least one compound having at least one silicon-hydrogen bond and
(D) at least one Ru(0)-sulfoxide complex catalyst of the formula (I).

3. The composition of claim 1 which is an addition-crosslinking composition comprising:
(i) at least one compound (A'), (B') or (C),
where
(A') is an organic compound, an organosilicon compound or mixtures thereof, the organic compound and organosilicon compound containing at least two radicals having aliphatic carbon-carbon multiple bonds,
(B') an organosilicon compound containing at least two Si-bonded hydrogen atoms and
(C) an organosilicon compound containing SiC-bonded radicals having aliphatic carbon-carbon multiple bonds and Si-bonded hydrogen atoms,
with the proviso that the composition contains at least one compound having aliphatic carbon-carbon multiple bonds and at least one compound having Si-bonded hydrogen atoms, and
(ii) at least one Ru(0)-sulfoxide complex catalyst (D) of the formula (I).

4. A crosslinked silicone elastomer obtained by addition-crosslinking of the composition of claim 3.

5. A coating obtained by addition-crosslinking of the composition of claim 3.

6. In a process for hydrosilylation wherein a hydrosilylation catalyst is employed, the improvement comprising employing a Ru(0) complex of formula (I) as a hydrosilylation catalyst

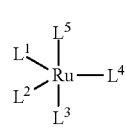
(I)

wherein
a) at least one of the ligands $L^1$-$L^5$ is a sulfoxide ligand of the formula (II)

$$R^1—S(=O)—R^2 \quad (II),$$

where the radicals $R^1$ and $R^2$ are identical or different and are selected independently from the group consisting of straight-chain and branched alkyl groups, alkenyl groups and alkynyl groups; straight-chain and branched alkyl groups, alkenyl groups and alkynyl groups having at least one substituent selected from the group consisting of alkoxy, siloxy, aryloxy, aryl, silyl, alkoxycarbonyl, aryloxycarbonyl, acyloxy, carboxamido, carbamoyl groups and halogen atoms; and phenyl groups which are substituted or unsubstituted, where substituents are selected from the group consisting of alkyl, alkenyl, alkynyl, silyl, alkoxy, siloxy, aryloxy, aryl, alkoxycarbonyl, aryloxycarbonyl, acyloxy, carboxamido and carbamoyl groups and halogen atoms;

and wherein $R^1$ and $R^2$ are optionally joined to form a heterocycle containing the sulfur atom or a heterocycle containing further heteroatoms, with the proviso that $R^1$ and $R^2$ together have 2-24 carbon atoms;

b) at least one of the ligands $L^1$-$L^5$ is a ligand which is π-bonded via one or two C=C functions and has the formula (III)

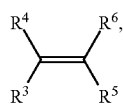
(III)

where the radicals $R^3$-$R^6$ are selected independently from the group consisting of hydrogen, straight-chain or branched, cyclic or acyclic, $C_1$-$C_{50}$-alkyl, $C_2$-$C_{50}$-alkenyl, $C_2$-$C_{50}$-alkynyl, and $C_6$-$C_{30}$-aryl radicals in which individual carbon atoms are unsubstituted or substituted by halogen, O, N, S, Si or P atoms, and c) remaining ligands $L^1$-$L^5$ are identical or different and are selected from the group consisting of uncharged 2-, 4- or 6-electron donor ligands containing CO; CNR''', where R''' is selected from the group consisting of alkyl and aryl; PR'''$_3$ and P(OR''')$_3$, where R''' is selected from the group consisting of alkyl and aryl; ligands containing N donors; ligands which contain S donors and do not correspond to the sulfoxides of formula (1); ligands containing O donors; and carbene ligands;

with the proviso that none of the ligands $L^1$-$L^5$ is 1,5-cyclooctadiene or 1,3,5-cyclooctatriene.

7. The process of claim 6, wherein the hydrosilylation is a polymerization.

* * * * *